United States Patent
Cabourg et al.

(10) Patent No.: US 9,320,694 B2
(45) Date of Patent: Apr. 26, 2016

(54) PROCESS FOR TREATING STRAIGHTENED KERATIN FIBRES

(75) Inventors: Julien Cabourg, Combs La Ville (FR); Gregory Plos, Paris (FR); Laetitia Feuillette, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/122,719

(22) PCT Filed: Jun. 1, 2012

(86) PCT No.: PCT/EP2012/060352
§ 371 (c)(1),
(2), (4) Date: Mar. 27, 2014

(87) PCT Pub. No.: WO2012/164064
PCT Pub. Date: Dec. 6, 2012

(65) Prior Publication Data
US 2014/0196741 A1    Jul. 17, 2014

Related U.S. Application Data

(60) Provisional application No. 61/528,642, filed on Aug. 29, 2011.

(30) Foreign Application Priority Data

Jun. 1, 2011    (FR) ...................................... 11 54804

(51) Int. Cl.
*A61K 8/365* (2006.01)
*A61K 8/362* (2006.01)
*A61Q 5/04* (2006.01)
*A61Q 5/00* (2006.01)
*A45D 7/06* (2006.01)

(52) U.S. Cl.
CPC . *A61K 8/365* (2013.01); *A45D 7/06* (2013.01); *A61K 8/362* (2013.01); *A61Q 5/00* (2013.01); *A61Q 5/04* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,060,680 | A * | 10/1991 | Akhtar | ........................... 132/204 |
| 8,309,067 | B2 * | 11/2012 | Devine et al. | ................. 424/70.2 |
| 8,906,352 | B2 * | 12/2014 | Malle et al. | ................... 424/70.2 |
| 2005/0048004 | A1 | 3/2005 | de la Guardia et al. | |
| 2010/0300471 | A1 | 12/2010 | Malle et al. | |
| 2013/0139844 | A1 | 6/2013 | Malle et al. | |
| 2013/0139845 | A1 | 6/2013 | Malle et al. | |

FOREIGN PATENT DOCUMENTS

| | | |
|---|---|---|
| EP | 0 011 511 A2 | 5/1980 |
| FR | 2 683 999 A1 | 5/1993 |
| JP | 02-295912 | 6/1990 |
| WO | 89/02233 A1 | 3/1989 |
| WO | 93/00882 A1 | 1/1993 |
| WO | 93/10751 A1 | 6/1993 |
| WO | 2006/011771 A1 | 2/2006 |
| WO | 2007/135299 A1 | 11/2007 |
| WO | 2010/049434 A2 | 5/2010 |

OTHER PUBLICATIONS www.folica.com/hair-101/tips-and-how-tos/how-to-flat-iron accessed online Nov. 12, 2014, available online Jan. 22, 2011.*
International Search Report for PCT/EP2012/060352.
Todd & Byers, "Volatile Silicone Fluids for Cosmetics," Cosmetics and Toiletries, vol. 91, Jan. 76, pp. 27-32.

* cited by examiner

*Primary Examiner* — Robert A Wax
*Assistant Examiner* — Melissa Mercier
(74) *Attorney, Agent, or Firm* — The Marbury Law Group, PLLC

(57) ABSTRACT

The present invention relates to a process for treating straightened keratin fibers, in which a composition comprising at least one carboxylic acid in its acid or salified form, the pH being greater than 8, is applied to the straightened keratin fibers.

18 Claims, No Drawings

PROCESS FOR TREATING STRAIGHTENED KERATIN FIBRES

CROSS REFERENCE TO RELATED APPLICATIONS

This is a national stage application of PCT/EP2012/060352, filed internationally on Jun. 1, 2012, which claims priority to U.S. Provisional Application No. 61/528,642, filed on Aug. 29, 2011, as well as French Application No. FR 1154804, filed on Jun. 1, 2011, all of which are incorporated herein by reference in their entireties.

The present invention relates to a process for treating keratin fibres, and in particular a process for treating straightened keratin fibres.

Two techniques are generally used to obtain permanent reshaping of the hair. They are based on breaking the —S—S— disulphide bonds present in keratin (cystine).

The first technique for permanently reshaping the hair consists, in a first stage, in opening the disulphide bonds using a composition containing a reducing agent (reduction step), and then, after having preferably rinsed the hair, in reconstituting said disulphide bonds, in a second stage, by applying to the hair, which has been placed under tension beforehand with rollers or the like or shaped or straightened by other means, an oxidizing composition, also known as fixative (oxidation step) so as to give the head of hair the desired shape.

This technique makes it possible, without distinction, either to wave the hair or to shape, straighten, relax or smooth it.

The second technique for obtaining permanent reshaping of the hair consists in performing an operation known as lanthionization, using a composition containing a base belonging to the hydroxide family. It results in the disulphide bonds (—CH$_2$—S—S—CH$_2$—) being replaced with lanthionine bonds (—CH$_2$—S—CH$_2$—).

The compositions generally used for carrying out the lanthionization contain, as base, a hydroxide such as sodium hydroxide, guanidinium hydroxide and lithium hydroxide.

Sodium hydroxide and guanidinium hydroxide are the main two agents used for shaping or straightening naturally frizzy hair.

Compared with the first technique previously described, using a reducing agent, this lanthionization technique does not require a fixing step since the formation of the lanthionine bridges is irreversible. It is therefore carried out in a single step. These two techniques make it possible either to wave the hair or to shape, straighten, relax or smooth it. However, the lanthionization technique is principally used for shaping naturally frizzy hair.

Treatments for long-lasting shaping of keratin fibres, and in particular hair-straightening treatments, cause considerable damage to the hair. In addition, the hair-straightening effectiveness is not always satisfactory. The hair-straightening is not perfect, the hair remains too voluminous and often exhibits frizziness that is persistent with respect to the hair-straightening treatment.

Post-treatment acid treatments are known to allow neutralization of the hair and the scalp after alkaline hair-straightening treatment.

A hair-straightening process in which a composition in the form of a mousse is applied to the straightened hair is known in particular from document US 2005/0048004, the styling mousse comprising a carboxylic acid, in particular 0.6% of glutamic acid or 0.4% of citric acid, the pH of the composition being between 3 and 8.

A hair-straightening process which comprises a step of acid rinsing of the straightened hair with a composition comprising between 0.1 and 5% by weight of an acid selected from citric acid, maleic acid, boric acid, lactic acid and phosphoric acid, between 0.1 and 5% by weight of a thickener chosen from hydroxyalkylcelluloses, between 0.1 and 10% of a wetting agent chosen from non-ionic surfactants, between 0.001 and 1% of a pH indicator and between 0.1 and 8% of laureth 23 as emulsifier, is also known from document WO09300882. The acid rinsing composition can also be applied between two applications of hair-straightening agents in order to temporarily smooth out new growth.

There is still a need to provide a process for treating keratin fibres which improves straightening of the fibre in a persistent manner and which reduces the overall volume of the hair.

The subject of the invention is therefore a process for treating straightened keratin fibres, in which a composition comprising at least one carboxylic acid in its acid or salified form, the pH being greater than 8, is applied to the straightened keratin fibres.

The term "straightened keratin fibres" is intended to mean keratin fibres that have undergone a straightening, relaxing or smoothing treatment using either a reducing agent or a hydroxide. When the straightened treatment uses a reducing agent, the term "straightened keratin fibres" is intended to mean keratin fibers having undergone the whole straightened treatment, namely the reduction's step and the oxidation's step by means of an oxidizing composition (fixative). Preferably, the straightened keratin fibres of the invention are fibres that have undergone a straightening treatment with a hydroxide.

The treatment process according to the invention makes it possible to reduce the overall volume of straightened hair, to reduce the hair mass effect, and to increase the persistence of the hair-straightening, and also makes it possible to obtain a feel without rough patches.

In the text hereinbelow, the term "at least one" is equivalent to the expression "one or more".

The composition used in the context of the process for treating straightened hair according to the invention comprises at least one carboxylic acid.

The term "carboxylic acid" is intended to mean simple carboxylic acids, polycarboxylic acids, in particular dicarboxylic acids, amino dicarboxylic acids, tricarboxylic acids, (poly)hydroxy(poly)carboxylic acids, in particular α-hydroxylated or dihydroxylated carboxylic acids, which can of course be used alone or as a mixture.

Preferably, the molecular weight of the carboxylic acid is lower than 250, better lower than 200.

As carboxylic acids that can be used in the compositions according to the invention, mention may more particularly be made of citric acid, maleic acid, succinic acid, aspartic acid, glutamic acid, lactic acid, malic acid and tartaric acid.

According to one particularly preferred embodiment of the process of the present invention, the acid used is citric acid.

The carboxylic acids used in the invention can be present in the composition, partially or totally, in the form of one of their salts. The salts that can be used can result from the combination of the acids of the invention with an organic or inorganic, and preferably inorganic, base.

Among the organic bases that may be mentioned are amines and in particular alkanolamines. Among the inorganic bases that may be mentioned are aqueous ammonia and alkali metal or alkaline-earth metal hydroxides. Preferably, the inorganic bases are alkali metal hydroxides and even more preferentially sodium hydroxide, resulting in sodium salts.

Among the salts of these acids that may be mentioned are sodium citrate, sodium maleate, sodium succinate, sodium aspartate, sodium glutamate, sodium lactate, sodium malate and sodium tartrate.

According to one particularly preferred embodiment of the process of the present invention, the acid salt used is sodium citrate.

The carboxylic acid(s) or carboxylic acid salt(s) are present in the composition in an amount from 1% to 50%, preferably from 1 to 10%, more preferably from 2 to 5%, the acid salt concentration being expressed in acid equivalent.

The composition generally comprises one or more solvents. These solvents may be chosen from water, $C_1$-$C_4$ alcohols, such as ethanol, isopropanol, tert-butanol, n-butanol, propylene carbonate, polyols such as propylene glycol, glycerol and polyol ethers, acetone, benzyl alcohol, and mixtures thereof.

Preferably, the composition is aqueous or aqueous-alcoholic, the preferred solvent being water.

The composition according to the invention may also comprise one or more surfactants. The surfactant(s) which can be used in the composition according to the invention can be chosen from cationic, anionic, non-ionic, amphoteric or zwitterionic non-silicone surfactants, silicone surfactants and mixtures thereof.

When a surfactant is present in the composition according to the invention, said composition preferably comprises at least 0.01% by weight of surfactant(s), relative to the total weight of the composition. Preferably, the composition according to the invention comprises from 0.05 to 20% by weight of surfactant(s), more preferably from 0.1 to 10% by weight and more preferably still from 0.5 to 5% by weight, relative to the total weight of the composition.

The composition according to the invention may also contain one or more fatty substances.

For the purpose of the present invention, the term "fatty substance" is intended to mean an organic compound which is insoluble in water at normal temperature (25° C.) and at atmospheric pressure (760 mmHg, i.e. $1.013 \times 10^5$ Pa), that is to say with a solubility of less than 4% by weight, preferably of less than 1% by weight and even more preferentially of less than 0.1% by weight. They have in their structure at least one hydrocarbon-based chain comprising at least 6 carbon atoms or a sequence of at least two siloxane groups. In addition, the fatty substances are soluble in organic solvents under the same temperature and pressure conditions, for instance chloroform, ethanol or benzene.

Preferably, the fatty substances of the invention are chosen from hydrocarbons, fatty alcohols, fatty esters, silicones and fatty ethers or their mixtures. They may be liquid or non-liquid at room temperature and at atmospheric pressure. The fatty substance(s) is (are) preferably present in an amount ranging from 0.1 to 30% by weight, preferably from 0.5 to 20% by weight and better still from 1 to 15% by weight, with respect to the total weight of the composition.

According to one particular embodiment, the composition contains a liquid fatty acid.

Advantageously, the liquid fatty substances are chosen from liquid alkanes, liquid fatty alcohols, liquid fatty acids, liquid fatty acid esters, liquid fatty alcohol esters, mineral, plant, animal or synthetic oils, and fluid silicones, or mixtures thereof.

It is recalled that, for the purpose of the invention, the fatty alcohols, esters and acids more particularly have at least one linear or branched, saturated or unsaturated hydrocarbon-based group comprising 6 to 30 carbon atoms, which is optionally substituted, in particular with one or more hydroxyl groups (in particular 1 to 4). If they are unsaturated, these compounds may comprise one to three conjugated or unconjugated carbon-carbon double bonds.

As regards the alkanes, these alkanes comprise from 6 to 30 carbon atoms and are linear or branched, optionally cyclic. Examples that may be mentioned include hexane, dodecane, undecane, tridecane or mixtures thereof.

As oils that may be used in the composition of the invention, examples that may be mentioned include:
  hydrocarbon-based oils of animal origin, such as perhydrosqualene;
  hydrocarbon-based oils of plant origin, such as liquid fatty acid triglycerides containing from 6 to 30 carbon atoms, for instance heptanoic or octanoic acid triglycerides, or alternatively, for example, sunflower oil, maize oil, soybean oil, marrow oil, grapeseed oil, sesame oil, hazelnut oil, apricot oil, macadamia oil, arara oil, castor oil, avocado oil, caprylic/capric acid triglycerides such as those sold by the company Stearineries Dubois or those sold under the names Miglyol® 810, 812 and 818 by the company Dynamit Nobel, jojoba oil and shea butter oil;
  linear or branched hydrocarbons of mineral or synthetic origin, such as volatile or non-volatile liquid paraffins, and derivatives thereof, petroleum jelly, liquid petroleum jelly, polydecenes, hydrogenated polyisobutene such as Parleam®; and isoparaffins, for instance isohexadecane and isodecane;
  partially hydrocarbon-based and/or silicone-based fluoro oils, for instance those described in document JP-A-2-295 912; fluoro oils that may also be mentioned include perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M;

As regards the liquid fatty alcohols, they are advantageously saturated or unsaturated, and linear or branched, and contain from 8 to 30 carbon atoms. Examples that may be mentioned include isostearyl alcohol, octyldodecanol, 2-butyloctanol, 2-hexyldecanol, 2-undecylpentadecanol, oleyl alcohol and linoleyl alcohol.

The liquid fatty acids may be saturated or unsaturated, and linear or branched, and contain from 6 to 30 carbon atoms and in particular from 9 to 30 carbon atoms. They are chosen more particularly from an oleic acid, linoleic acid, linolenic acid and isostearic acid. In order to be considered as fatty substances in the compositions, the fatty acids must not be in the form of soaps, i.e. they must not be salified with an organic or inorganic base.

The esters are preferably esters of saturated or unsaturated, linear or branched $C_{10}$-$C_{26}$ aliphatic monoacids or polyacids and of saturated or unsaturated, linear or branched $C_1$-$C_6$ aliphatic monoalcohols or polyalcohols.

Among the monoesters, mention may be made of ethyl and isopropyl palmitates, and alkyl myristates such as isopropyl myristate or ethyl myristate.

Still within the context of this variant, esters of $C_4$-$C_{22}$ dicarboxylic or tricarboxylic acids and of $C_1$-$C_{22}$ alcohols and esters of monocarboxylic, dicarboxylic or tricarboxylic acids and of $C_2$-$C_{26}$ dihydroxy, trihydroxy, tetrahydroxy or pentahydroxy alcohols may also be used.

Mention may be made in particular of: diethyl sebacate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; octyl isononanoate; and isononyl isononanoate.

Among the esters mentioned above, ethyl and isopropyl palmitates, alkyl myristates such as isopropyl or butyl myristate, dioctyl malate and isononyl isononanoate are preferably used.

The silicones that can be used in the cosmetic compositions of the present invention are volatile or non-volatile, cyclic, linear or branched silicones, which are unmodified or modified with organic groups, having a viscosity from $5\times10^{-6}$ to 2.5 m²/s at 25° C., and preferably $1\times10^{-5}$ to 1 m²/s.

The silicones that can be used in accordance with the invention are in the form of oils. Preferably, the silicone is chosen from polydialkylsiloxanes, in particular polydimethylsiloxanes (PDMSs), and organomodified polysiloxanes comprising at least one functional group chosen from poly(oxyalkylene) groups, amino groups and alkoxy groups.

Organopolysiloxanes are defined in greater detail in Walter Noll's "Chemistry and Technology of Silicones" (1968), Academic Press. They may be volatile or non-volatile.

When they are volatile, the silicones are more particularly chosen from those having a boiling point of from 60° C. to 260° C., and even more particularly from:
(i) cyclic polydialkylsiloxanes containing from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

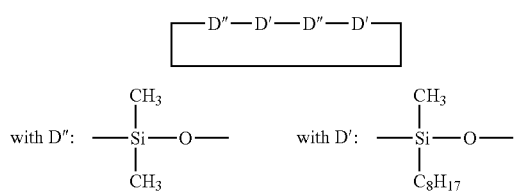

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;
(ii) linear volatile polydialkylsiloxanes containing 2 to 9 silicon atoms and having a viscosity of less than or equal to $5\times10^{-6}$ m²/s at 25° C. An example is decamethyltetrasiloxane sold in particular under the name SH 200 by the company Toray Silicone. Silicones belonging to this category are also described in the article published in Cosmetics and Toiletries, Vol. 91, Jan. 76, P. 27-32—TODD & BYERS "Volatile Silicone fluids for cosmetics".

Use is preferably made of non-volatile polydialkylsiloxanes, polydialkylsiloxane gums and resins, polyorganosiloxanes modified with the organofunctional groups above, and mixtures thereof.

These silicones are more particularly chosen from polydialkylsiloxanes, among which mention may be made mainly of polydimethylsiloxanes having trimethylsilyl end groups. The viscosity of the silicones is measured at 25° C. according to ASTM standard 445 Appendix C.

Among these polydialkylsiloxanes, mention may be made, in a nonlimiting manner, of the following commercial products:
the Silbione® oils of the 47 and 70 047 series or the Mirasil® oils sold by Rhodia, for instance the oil 70 047 V 500 000;
the oils of the Mirasil® series sold by the company Rhodia;
the oils of the 200 series from the company Dow Corning, such as DC200 with a viscosity of 60 000 mm²/s;
the Viscasil® oils from General Electric and certain oils of the SF series (SF 96, SF 18) from General Electric.

Mention may also be made of polydimethylsiloxanes having dimethylsilanol end groups known under the name dimethiconol (CTFA), such as the oils of the 48 series from the company Rhodia.

The organomodified silicones that can be used in accordance with the invention are silicones as defined above and comprising in their structure one or more organofunctional groups attached via a hydrocarbon-based group.

Besides the silicones described above, the organomodified silicones may be polydiarylsiloxanes, in particular polydiphenylsiloxanes, and polyalkylarylsiloxanes functionalized with the organofunctional groups mentioned previously.

The polyalkylarylsiloxanes are chosen particularly from linear and/or branched polydimethyl/methylphenylsiloxanes and polydimethyl/diphenylsiloxanes with a viscosity of from $1\times10^{-5}$ to $5\times10^{-2}$ m²/s at 25° C.

Among these polyalkylarylsiloxanes, examples that may be mentioned include the products sold under the following names:
the Silbione® oils of the 70 641 series from Rhodia;
the oils of the Rhodorsil® 70 633 and 763 series from Rhodia;
the oil Dow Corning 556 Cosmetic Grade Fluid from Dow Corning;
certain oils of the SF series from General Electric, such as SF 1023, SF 1154, SF 1250 and SF 1265.

The composition according to the invention can also comprise one or more thickeners which can be chosen from polymeric thickeners which are natural or synthetic, anionic, amphoteric, zwitterionic, non-ionic or cationic and associative or non-associative, and non-polymeric thickeners, such as, for example, an electrolyte or a sugar.

Mention may be made, as polymeric thickeners, for example, of cellulosic thickeners, for example hydroxyethylcellulose, hydroxypropylcellulose and carboxymethylcellulose, guar gum and its derivatives, for example hydroxypropyl guar, sold by Rhodia under the reference Jaguar HP 105, gums of microbial origin, such as xanthan gum and scleroglucan gum, synthetic polymeric thickeners, such as crosslinked homopolymers of acrylic acid or of acrylamidopropanesulphonic acid, for example Carbomer, or non-ionic, anionic or amphoteric associative polymers, such as the polymers sold under the names Pemulen TR1 or TR2 by the company Goodrich, Salcare SC90 by the company Allied Colloids, Aculyn 22, 28, 33, 44 or 46 by the company Rohm & Haas and Elfacos T210 and T212 by the company Akzo.

The composition of the invention may also contain one or more fixing polymers. For the purpose of the invention, the term "fixing polymer" is intended to mean any polymer which makes it possible to shape or retain the shape of the hair.

The composition used in the process of the invention has a pH of greater than 8, preferably ranging from 8.01 to 13, more preferably from 8.01 to 10, better still from 8.01 to 9, and even better still from 8.1 to 9.

The composition may comprise pH adjusters other than the carboxylic acids of the invention. The pH adjusters may be acidifying or basifying agents.

Among the acidifying agents, mention may be made, by way of example, of mineral or organic acids, such as hydrochloric acid, orthophosphoric acid, sulphuric acid, or sulphonic acids.

The composition preferably comprises at least one basifying agent.

Mention may be made, among the basifying agents, by way of example, of aqueous ammonia, alkaline carbonates, alkanolamines, such as mono-, di- and triethanolamines, and derivatives thereof, sodium hydroxide, potassium hydroxide and the compounds of the following formula:

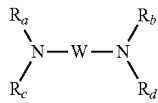

in which W is a propylene residue optionally substituted with a hydroxyl group or a $C_1$-$C_4$ alkyl radical; $R_a$, $R_b$, $R_c$ and $R_d$, which may be identical or different, represent a hydrogen atom or a $C_1$-$C_4$ alkyl or $C_1$-$C_4$ hydroxyalkyl radical.

Preferably, the pH adjusters may be chosen from aqueous ammonia, monoethanolamine, diethanolamine, triethanolamine, 1,3-propanediamine and an alkaline hydroxide, such as 2-amino-2-methyl-1-propanol.

The composition of the invention may be in the form of a foam, a gel, a serum, a liquid lotion or a lacquer.

The composition may be packaged in a pump-dispenser bottle or in an aerosol device.

When it is packaged in an aerosol-type device, the liquid phase/propellant weight ratio of the pressurized composition of the present invention is going preferably from 50 to 0.05, and in particular from 50 to 1.

For the aerosol formulations, any halogenated or non-halogenated, volatile alkane which is customarily used in aerosol devices will be used as propellant gas.

Preferably, the compound(s) constituting the propellant gas used is (are) chosen from non-halogenated $C_3$-$C_5$ alkanes, such as propane, n-butane and isobutane, halogenated, and in particular chlorinated and/or fluorinated, $C_3$-$C_5$ alkanes, such as 1,1-difluoroethane, and mixtures thereof.

According to a particularly preferred embodiment, said alkane(s) of the propellant gas is (are) non-halogenated. Even more preferably, the propellant gas is a mixture of propane, n-butane and isobutane.

In the case of aerosol foams, the composition introduced into the aerosol device may, for example, be in the form of a lotion, or dispersions or emulsions which, after dispensing from the aerosol device, form foams to be applied to keratin substances.

These foams must be sufficiently stable not to rapidly liquefy and must also rapidly disappear, either spontaneously or during the massaging which is used to cause the composition to penetrate into keratin substances and/or to distribute the composition over keratin substances and more particularly the head of hair and/or the hair.

For the aerosol formulations, the propellant may be any liquefiable gas customarily used in aerosol devices. Dimethyl ether, $C_3$-$C_5$ alkanes, chlorinated and/or fluorinated hydrocarbons such as 1,1-difluoroethane, and mixtures thereof, for instance mixtures of dimethyl ether and of $C_3$-$C_5$ alkanes, and mixtures of 1,1-difluoroethane and of dimethyl ether and/or of $C_3$-$C_5$ alkanes, are in particular chosen. Carbon dioxide, nitrous oxide, nitrogen or compressed, or mixtures thereof, air may also be used as propellant.

Preferably, the propellant gas used is dimethyl ether or $C_3$-$C_5$ alkanes, and in particular propane, n-butane and isobutane, and mixtures thereof.

The propellant gas is present in the composition according to the invention in proportions preferably ranging from 1 to 99% by weight, more preferentially from 1.5 to 50% by weight and better still from 2 to 30% by weight, relative to the total weight of the composition.

The aerosol device used to package the composition of the invention may be made up of two compartments, formed from an outer aerosol can comprising an inner bag hermetically sealed to a valve. The composition is introduced into the inner bag and a compressed gas is introduced between the bag and the can at a pressure sufficient to make the product come out in the form of a spray through a nozzle orifice. Such a device is sold, for example, under the name EP Spray by the company EP-Spray System SA. The said compressed gas is preferably used at a pressure of from 1 to 12 bar and better still from 9 to 11 bar.

The composition according to the invention can be applied at ambient temperature or with a contribution of heat, for example using a hairdryer, a hood or a smoothing iron of flat tongs.

The composition according to the invention may also contain one or more adjuvants chosen from polymers, including the thickening polymers mentioned above, ceramides and pseudoceramides, vitamins and pro-vitamins, including panthenol, silicone or non-silicone, water-soluble and liposoluble sunscreens, pearlescent agents and opacifiers, sequestering agents, conditioning agents, such as in particular cationic polymers, solubilizing agents, antioxidants, penetrating agents, fragrances, peptizers, preservatives, direct and oxidation dyes, organic or mineral pigments, agents for long-lasting shaping of the hair (thiol organic reducing agents, non-thiol organic reducing agents, alkaline agents, etc), and any other additive conventionally used in the cosmetics field.

A person skilled in the art will take care to choose the optional additives and amounts thereof so that they do not interfere with the properties of the compositions of the present invention. These additives may be present in the composition according to the invention in an amount ranging from 0 to 20% by weight relative to the total weight of the composition.

According to the invention, a composition comprising at least one carboxylic acid in its acid or salified form, the pH being greater than 8, is applied to straightened hair at ambient temperature (preferably at a temperature from 22 to 27° C.).

In a preferred variant, the straightened hair was straightened beforehand using a hair-straightening composition containing an alkaline agent, in particular sodium hydroxide or guanidine. The hair-straightening composition containing an alkaline agent may be any professional or public commercial hair-straightening agent based on sodium hydroxide or guanidine (Dark and Lovely or Soft Sheen Carson are the preferred hair-straightening agents). They may be of different strengths: resistant hair (strong), slightly sensitized hair (regular) or very sensitized hair (mild).

After the hair-straightening, the hair is rinsed with water and optionally washed with a shampoo.

The composition for treating straightened hair is then applied to wet or dry hair. The composition is preferably applied to wet hair. When it is applied to dry hair, the hair has been dried with a hairdryer or with a hood or air-dried.

The composition is left on the hair for a period of time ranging from 5 min to 2 hours, preferably for a period of time ranging from 5 to 30 min, preferably for a period of time ranging from 10 to 30 min, more preferably for approximately 20 min. During the leave-on time of the treatment, the hair may optionally be covered with a towel, a scarf, or any other covering, and heat may optionally be maintained on the hair by means of a hood or a hairdryer.

The hair may subsequently be rinsed and then washed with a shampoo. The hair is subsequently dried with a hairdryer or a hood or air-dried.

Another care treatment may be applied before or after the composition according to the invention.

The process according to the invention may also comprise a step of smoothing the hair with a smoothing iron. The smoothing iron is preferentially passed over semi-dry hair at the end of treatment in order to finalize the aesthetic quality of the hairstyle.

The application can be repeated as many times as necessary following hair-straightening, after each shampooing procedure, each day, or only after each hair-straightening treatment.

Concrete examples illustrating the invention will now be given.

In order to prepare the borax buffer solution at pH 8.2, 100 ml of $Na_2B_4O_7 \cdot 10H_2O$ at 0.025 M and 37.6 ml of HCl at 0.1 M are, for example, mixed together.

An entire head of frizzy hair of afro type is treated with an alkaline hair-straightening product containing guanidine, sold under the name Dark and Lovely Moisture System No-lye, regular, with a leave-on time of 20 minutes. The hair-straightening treatment is rinsed off with water.

The composition of example 2 which comprises sodium citrate is applied to half a head. One of the compositions of comparative examples 7, 8 or 9 which does not comprise sodium citrate is applied to the other half of the head. It is left on for 20 minutes. The hair is then partially dried with a hairdryer for 5 minutes. A smoothing iron is passed over each lock twice, over the whole of the head of hair.

A clear difference in results is then observed between the treatment using the composition of example 2 and those using the compositions of examples 7, 8 or 9: the hair treated with the composition of example 2 is more flattened against the roots, much less voluminous overall, and has a more pleasant feel, without rough patches.

The invention claimed is:

1. A process for treating straightened keratin fibers, said process comprising a step of:
   applying to the straightened keratin fibers a composition comprising at least one carboxylic acid in its acid or salified form in an amount ranging from 1% to 50%, wherein the molecular weight of the carboxylic acid is lower than 250,
   wherein the pH of the composition is greater than about 8.

2. The process according to claim 1, wherein the composition comprises at least one carboxylic acid chosen from tricarboxylic acids or salts thereof, dicarboxylic acids or salts thereof, amino dicarboxylic acids or salts thereof, monocar-

TABLE 1

| Composition | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| Citric acid | 2 | — | 5 | — | — | — | — | — | — |
| Sodium citrate | — | 2 | — | 5 | — | — | — | — | — |
| X * | — | — | — | — | 1.5 | 5 | — | — | — |
| Phosphate buffer pH 12 | — | — | — | — | — | — | $Na_2HPO_4$ 0.05M + NaOH 0.1M qs pH 12 | — | — |
| Carbonate buffer pH 9.5 | — | — | — | — | — | — | — | $NaHCO_3$ 0.05M + NaOH 0.1M qs pH 9.5 | — |
| Borax buffer pH 8.2 | — | — | — | — | — | — | — | — | $Na_2B_4O_7 \cdot 10 H_2O$ 0.025M + HCl 0.1M qs pH 8.2 |
| Preservatives | 1.3 | 1.3 | 1.3 | 1.3 | 1.3 | 1.3 | 1.3 | 1.3 | 1.3 |
| Castor oil | 1.6 | 1.6 | 1.6 | 1.6 | 1.6 | 1.6 | 1.6 | 1.6 | 1.6 |
| pH adjuster if necessary (NaOH in particular) | qs pH ≥ 8.1 | qs pH ≥ 8.1 | qs pH ≥ 8.1 | qs pH ≥ 8.1 | qs pH ≥ 8.1 | qs pH ≥ 8.1 | | | |
| Water | qs | qs | qs | qs | qs | qs | qs | qs | qs |

* X: acids tested: maleic acid, sodium maleate, succinic acid, sodium succinate, aspartic acid, sodium aspartate, glutamic acid, sodium glutamate, lactic acid, sodium lactate, malic acid, sodium malate, tartaric acid, sodium tartrate.

In order to prepare the phosphate buffer solution at pH 12, 100 ml of $Na_2HPO_4$ at 0.05 M are, for example, mixed with 53.8 ml of NaOH at 0.1 M.

In order to prepare the carbonate buffer solution at pH 9.5, 100 ml of $NaHCO_3$ at 0.05 M are, for example, mixed with 10 ml of NaOH at 0.1 M or of $Na_2CO_3$ at 1 M and HCl at 37%, qs pH 9.5.

boxylic acids or salts thereof, α-hydroxylated carboxylic acids or salts thereof, and dihydroxylated carboxylic acids or salts thereof.

3. The process according to claim 1, wherein the composition comprises at least one carboxylic acid or one carboxylic acid salt chosen from citric acid, sodium citrate, maleic acid, sodium maleate, succinic acid, sodium succinate, aspartic acid, sodium aspartate, glutamic acid, sodium glutamate, lactic acid, sodium lactate, malic acid, sodium malate, tartaric acid and sodium tartrate.

4. The process according to claim 1, wherein the carboxylic acid is chosen from citric acid and salts thereof.

5. The process according to claim 1, wherein the composition comprises carboxylic acid in acid or salified form in an amount ranging from about 1% to about 10%.

6. The process according to claim 1, wherein the composition comprises carboxylic acid in acid or salified form in an amount ranging from about 2% to about 5%.

7. The process according to claim 1, wherein the composition further comprises at least one basifying agent.

8. The process according to claim 7, wherein the basifying agent is chosen from aqueous ammonia; alkaline carbonates; alkanolamines, mono, di- and triethanolamines and derivatives thereof; sodium hydroxide; potassium hydroxide; compounds of the following formula:

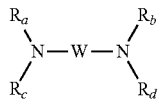

wherein W is a propylene residue optionally substituted with a hydroxyl group or a $C_1$-$C_4$ alkyl radical; $R_a$, $R_b$, $R_c$ and $R_d$, which may be identical or different, represent a hydrogen atom or a $C_1$-$C_4$ alkyl or $C_1$-$C_4$ hydroxyalkyl radical; and mixtures thereof.

9. The process according to claim 1, wherein the composition has a pH ranging from about 8.01 to about 13.

10. The process according to claim 1, wherein the composition has a pH ranging from about 8.01 to about 10.

11. The process according to claim 1, wherein the composition has a pH ranging from about 8.01 to about 9.

12. The process according to claim 1, wherein the composition has a pH ranging from about 8.1 to about 9.

13. The process according to claim 1, further comprising leaving the composition on the keratin fibers for a period of time ranging from about 5 minutes to about 2 hours.

14. The process according to claim 1, further comprising leaving the composition on the keratin fibers for a period of time ranging from about 5 to about 30 minutes.

15. The process according to claim 1, further comprising leaving the composition on the keratin fibers for a period of time ranging from about 10 to about 30 minutes.

16. The process according to claim 1, wherein the keratin fibers have been straightened beforehand by applying a composition comprising an alkaline hydroxide.

17. The process according to claim 1, wherein the composition is applied to wet hair.

18. The process according to claim 1, further comprising smoothing the hair with a smoothing iron.

* * * * *